United States Patent [19]
Grob et al.

[11] Patent Number: 5,779,765
[45] Date of Patent: Jul. 14, 1998

[54] PROCESS AND DEVICE FOR THE INJECTION OF LARGE VOLUMES OF LIQUID SAMPLES IN A GASCHROMATOGRAPH

[75] Inventors: Konrad Grob, Fehraltorf, Switzerland; Fausto Munari, Milan, Italy

[73] Assignee: Thermoquest Italia S.P.A., Milan, Italy

[21] Appl. No.: 679,255

[22] Filed: Jul. 12, 1996

[30] Foreign Application Priority Data

Jul. 14, 1995 [IT] Italy ............................... MI95A1507

[51] Int. Cl.$^6$ ................................................ B01D 15/08
[52] U.S. Cl. ............... 95/83; 95/86; 95/87; 96/105; 73/23.41
[58] Field of Search ............... 95/82–89; 96/101–109; 73/19.02, 23.35, 23.41, 61.52, 61.56

[56] References Cited

U.S. PATENT DOCUMENTS

| | | | |
|---|---|---|---|
| 3,225,520 | 12/1965 | Burow | 95/87 |
| 3,225,521 | 12/1965 | Burow | 95/87 X |
| 3,860,393 | 1/1975 | Campen, Jr. | 73/23.1 X |
| 3,881,892 | 5/1975 | Gehrke et al. | 95/86 |
| 4,007,626 | 2/1977 | Roof et al. | 73/23.1 |
| 4,383,839 | 5/1983 | Sisti et al. | 95/83 |
| 4,477,266 | 10/1984 | Yang et al. | 95/89 X |
| 4,734,107 | 3/1988 | Trestianu et al. | 95/87 |
| 4,805,441 | 2/1989 | Sides et al. | 95/87 X |
| 4,849,179 | 7/1989 | Reinhardt et al. | 95/89 X |
| 5,048,322 | 9/1991 | Hiller et al. | 73/23.41 |
| 5,057,126 | 10/1991 | Lubkowitz et al. | 55/67 |
| 5,096,471 | 3/1992 | Sacks et al. | 95/87 |
| 5,135,549 | 8/1992 | Phillips et al. | 95/83 X |
| 5,141,532 | 8/1992 | Sacks et al. | 95/87 |
| 5,163,979 | 11/1992 | Patrick et al. | 95/82 X |
| 5,288,310 | 2/1994 | Peters et al. | 96/104 |
| 5,547,497 | 8/1996 | Klemp et al. | 95/85 X |
| 5,588,988 | 12/1996 | Gerstel et al. | 96/101 |

FOREIGN PATENT DOCUMENTS

| | | |
|---|---|---|
| 0 189 862 | 8/1986 | European Pat. Off. |
| 0 461 438 A2 | 12/1991 | European Pat. Off. |
| 2 637 685 | 4/1990 | France |

*Primary Examiner*—Robert Spitzer
*Attorney, Agent, or Firm*—Millen, White, Zelano & Branigan, P.C.

[57] ABSTRACT

To inject a liquid sample with large volume into a GC column of a gas chromatograph, its volatile portion is evaporated by heat, in a non-selective way, in a vaporization chamber, the vapors thus generated being fed to pre-column located upstream of the GC column and maintained at a lower temperature to that of the vaporization chamber, where such compounds are separated from the solvent vapors, which are unloaded into the atmosphere while the compounds to be analyzed are sent to the GC column.

15 Claims, 2 Drawing Sheets

PROCESS AND DEVICE FOR THE INJECTION OF LARGE VOLUMES OF LIQUID SAMPLES IN A GASCHROMATOGRAPH

FIELD OF THE INVENTION

The present invention relates to a process and a device for the introduction of large volumes (with flows up to 800–1000 µl/min or more) of liquid samples in gaschromatography columns, in capillary columns in particular.

The introduction of large volumes of sample into a GC capillary column involves substantially two phases: the evaporation of the solvent and its separation from the compounds of interest. These compounds must be evaporated and sent to the GC column, while the large volume of solvent vapor must be unloaded before reaching the GC column, without at the same time losing any of the volatile compounds in the sample.

The use of a "retention gap" (a length of tube upstream of the GC column, deprived of stationary phase, where the sample was evaporated simultaneously with or subsequently to its arrival) was initially proposed to obtain such results. Later, a PTV type evaporation chamber was proposed, in which the sample is present partly in the liquid state during the evaporation of the solvent. In both cases, most of the evaporated solvent is unloaded before entering the GC column.

One of the various problems of these techniques is that of avoiding the loss of the volatile compounds together with the solvent vapor. For this reason, it was proposed to inject the sample onto a pre-column (retention gap) maintained at a temperature below or slightly above that of evaporation of the solvent, to obtain initially only the evaporation of the latter. However, this solution has the disadvantage of taking a long time and requiring a bulky interface. Besides, this solution is not feasible when the solvent is of the non-wetting type, i.e. it doesn't form a layer on the walls of the pre-column and does not give the required compound retention through the solvent effect.

Alternatively, injection of the sample into a hot vaporization chamber provided with packing was proposed, at such a flow-rate as to ensure the presence of liquid solvent in the chamber during its evaporation, for the purpose of holding back the compounds to be analyzed due to the "solvent effect". This solution also has not proven fully satisfactory.

Other problems encountered in these techniques are due to the presence in the sample of non-volatile compounds, which degrade and contaminate the pre-column.

OBJECTS OF THE INVENTION

One object of the present invention is to resolve the above-mentioned problems with a process for the introduction for vaporization of liquid samples into a capillary GC column that allows the elimination of solvent vapors without the loss of the compounds of interest present; which avoids the contamination of the GC column, and which makes it possible to analyse samples with non-wetting solvents.

Another object of the invention is to furnish a device to carry out the above process.

SUMMARY OF THE INVENTION

Such objects are achieved by the present invention, which relates to a process for the introduction of liquid samples into a gaschromatograph comprising the evaporation of the sample before sending the compounds into the column.

The invention also relates to a device for the introduction of liquid samples into a gaschromatograph, comprising a vaporization chamber.

Contrary to what has been produced or suggested in the present art, the sample is evaporated in non-selective way, i.e. no effort is made to evaporate only the solvent initially and hold back the compounds of interest in the vaporization chamber. On the contrary, the solvent vapors and the compounds of interest are selected by the means of retention set downstream of the vaporization chamber, holding back the compounds to be analyzed and unloading the solvent vapors.

According to a first embodiment of the invention, the compounds of interest undergo retention in a pre-column provided with a stationary phase. The coated pre-column is maintained at the minimum temperature to avoid the solvent vapor recondensing: in this way "phase soaking"—a "swelling" of the stationary phase—is obtained which allows retention of the volatile compounds even in the absence of a solvent effect, i.e. in the absence of liquid solvent. Subsequently, the pre-column is heated and the compounds sent to the GC column.

According to another embodiment of the invention, the retention of the compounds of interest is achieved by recondensing the sample in whole or in part (depending on the injected volume) in a pre-column deprived of stationary phase (retention gap) so as to have retention by solvent effect. As in the preceding case, the pre-column is subsequently heated to send the compounds to the GC column. The two techniques could coexist, i.e. there could be an initial recondensation of the vapors of the sample in a non-coated pre-column, then the vapors could be made to flow out of this and go through a pre-column coated with a stationary phase.

According to another aspect of the invention, the rate at which the liquid sample is sent to the vaporization chamber is controlled.

According to a further aspect of the invention, inside the vaporization chamber is a physical means of stabilizing the evaporation front of the injected liquid sample, during the evaporation of the same. In fact, the temperature of the vaporization chamber would provoke a violent forward and backward movement of the liquid sample inside of the same chamber, which is generally also constituted by a pre-column. In a preferential embodiment, such means comprises a thread or a fiber of inactive material, e.g. metal or fused silica (deactivated). Alternatively, an inert material packing is used.

The invention presents numerous advantages with respect to the present art.

A first advantage is given by independently heating the vaporization chamber and the gaschromatograph oven. This allows lower pre-column temperatures than those possible according to the present art, while introducing large quantities of liquid sample into the vaporization chamber quickly, with flow-rates at least up to 800 µl/min for dichloromethane-type solvents, up to 300 µl/min for aqueous solvents such as water/methanol and up to 1700 µl/min for pentane and similar solvents. It is thus possible to raise the lower limits of revelation of the compounds.

A third advantage is given by the fact that the separation of solvent from compounds to be analyzed operates on their vapors. This allows the regulation of the temperature in the pre-column where this separation takes place to be regulated, and the optimization of the conditions of "phase soaking" (FIG. 5).

Another advantage is given by the high percentage of volatile compounds retained and sent on to analysis.

A further advantage consists in the fact that the evaporation front is stabilized. i.e. that the liquid sample doesn't wet the GC column. In this way the non-volatile compounds present in the sample (i.e. its non-volatile portion) stays trapped in the vaporization chamber, without contaminating either the column or pre-column.

Another advantage is given (in the version that provides "phase soaking") by the possibility of injecting non-wetting liquids, such as fractions deriving from a LC "reversed-phase" analysis.

BRIEF DESCRIPTION OF THE DRAWINGS

The invention will now be illustrated in more detail with reference to the enclosed drawings which are illustrative and not limiting. and in which:

The FIG. 1 is a scheme of an embodiment of the device according to the invention;

Figure 1:
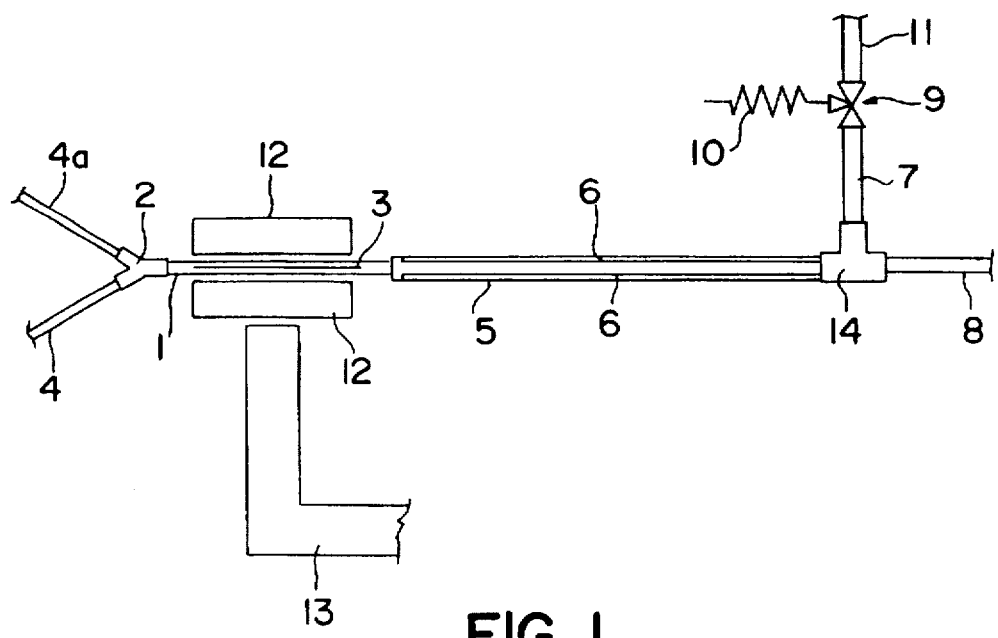
Figure 2:
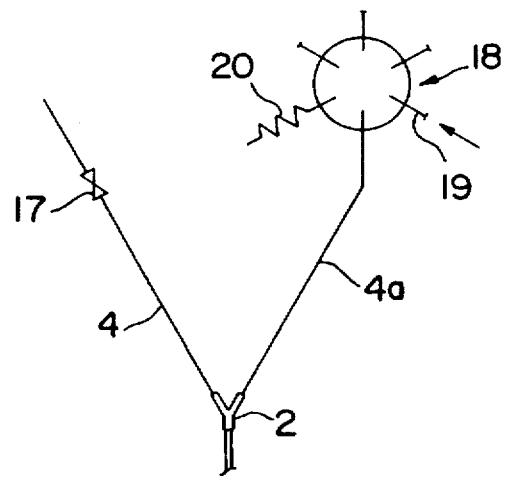
Figure 4:
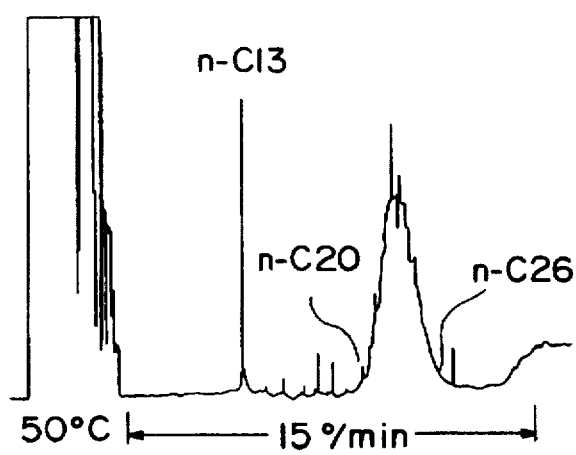
Figure 3:
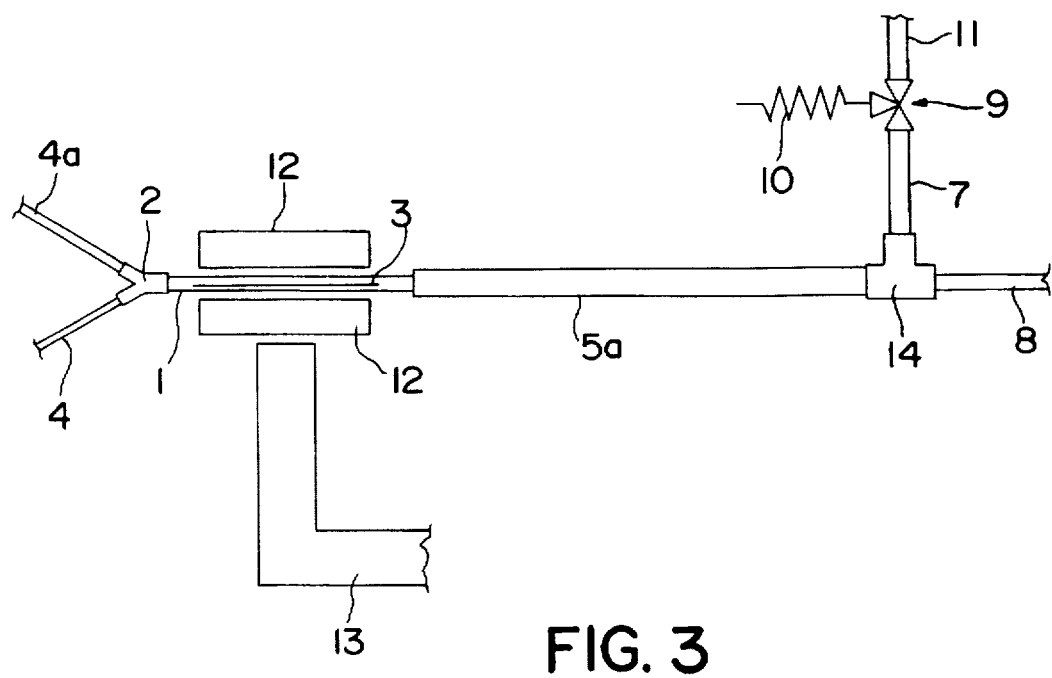
Figure 5:
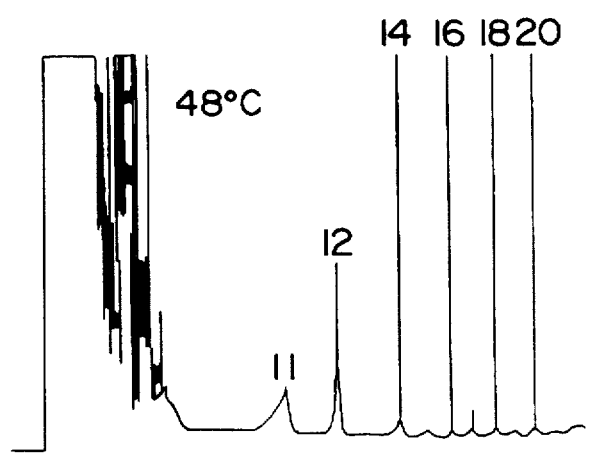

The FIG. 2 is a schematic view of an interface between a LC pump and the vaporization chamber of the device in FIG. 1;

The FIG. 3 is a scheme of a further embodiment of the invention;

The FIG. 4 shows the chromatogram of an analysis effected according to the invention; and The FIG. 5 shows the chromatogram of an analysis with "phase soaking."

DESCRIPTION OF THE PREFERRED EMBODIMENTS

The device shown in FIG. 1 comprises a solvent vaporization chamber 1, formed in this case by a capillary tube in fused silica with internal diameter of 0.32 mm and length 5–7 cm. The chamber 1 is connected upstream with a connector 2, to which is fixed a sample feed line 4a from an interface valve (see FIG. 2) and a transport-gas feed line 4.

Downstream, the chamber 1 is connected to a pre-column 5, for instance a capillary column in fused silica with internal diameter 0.53 mm. The pre-column 5 is internally coated with a stationary phase 6 and the end is connected, through a "T-piece" 14, with a solvent-vapor unloading duct 7 and with the opening of the GC separation column 8. The unloading duct 7 is fitted with a valve 9, which allows it to be connected alternatively to an unloading duct 11 with substantially no resistance during the unloading of the vapors, or to a capillary resistance 10, to unload interrupted vapors.

The vaporization chamber 1 is fitted with a means of heating 12, separate and distinct from the means of heating the pre-column 5, which is generally the gaschromatograph oven 13. This configuration mirrors the fact that the chamber 1 is maintained at a temperature very much greater than that of the boiling point of the solvent, generally to at least 200° C., while the pre-column is kept to the lowest temperature which prevents the condensation of the solvent and thus interacts the solvent vapors with the stationary phase 6 (phase soaking) so swelling it and increasing the power of retention.

Inside of the chamber 1 there is a means 3 of stabilizing the evaporation front of the liquid sample entering the vaporization chamber. The temperature of the chamber 1 is such as to prevent the liquid sample from accumulating inside the chamber to the point of escaping and flooding the pre-column 5. In other words, a means of stabilization serves to avoid a violent and uncontrolled evaporation of the solvent and the so-called "shooting" of the same, i.e. a forward and backward movement of a plug of liquid in chamber 1, under the effect of the pressure of the vapors of solvent which are being formed.

The means 3 comprises a packing of inert material with upper and lower "plugs" in glass wool or a full element inserted in chamber 1. It has been ascertained—surprisingly—that a thread or fiber in metal or a capillary in fused silica, closed at the extremities, treated in such a way to become inactive, eliminates the "shooting" and allows sample feeding with flow-rates more elevated than those otherwise possible. These full tubular elements have external diameters preferably larger than means the internal diameter of the vaporization chamber; for instance, for a chamber comprising a capillary with internal diameter of 0.32 mm an insert is used with external diameter between 0.19 and 0.29 mm. With regard to the inert packing, this presents the advantage of having a smaller, geometrically simpler surface and is, therefore, a better retainer.

In the vaporization chamber there is no means of temporary retention of the compounds e.g. a stationary phase on the inert material or on the thread-like insert, in as far as the sample is vaporized simultaneously with its introduction without substantially discriminating between solvent and compound, as happened in the preceding art. The embodiment shown in FIG. 3 refers to a version of the invention in which a means of retention of the compounds is constituted by a pre-column 5a, deprived of stationary phase, disposed between the vaporization chamber 1 and the capillary column 8 and connected to the latter via the link 14 having the unloading duct 7.

The purpose of the pre-column 5a is to allow recondensation of at least part of the solvent vapors to trap the compounds of interest through the solvent effect. Therefore, in this case, the temperature of the pre-column 5a will be regulated to give the desired recondensation of the solvent without at the same time flooding the pre-column 5a.

This embodiment could be combined with that of FIG. 1, to give a device which in this case presents, in the following order, the chamber 1, the pre-column 5a, the pre-column 5, the duct 7 and the GC capillary column 8. The FIG. 2 shows an embodiment of an interface for the device according to the invention, i.e. its portion upstream of the vaporization chamber 1.

As can be seen, the duct 4 is fitted with a valve 17 intercepting the transport gas, and the duct 4a is fitted with a valve 18 to control the feeding of liquid sample along the line 19 from a means of supply. Generally, the liquid sample arrives from a liquid chromatography apparatus or from a sampler.

In more detail, the valve 18 connects the duct 4a directly with the line 19 and a LC apparatus or a sampler, which provide for pushing the sample into the vaporization chamber with the required flow-rate. In this way, the flow of liquid sample is controlled, which is a preferential characteristic of the present invention.

There is a resistance 20 provided to reduce the countercurrent "backflush" during the analysis.

The device operates in the following way.

A first separation is effected in the LC (or HPLC) apparatus. The valve 19 is set in the configuration to dispatch the unloading of the eluent in arrival from the LC column. When the fraction containing the sample to be analyzed comes off the column, it is sent through the line 19 to the valve 18, which is set to dispatch the fraction directly to the duct 4a and to the vaporization chamber 1. Alternatively, the liquid sample is sent to the chamber 1 in another way, for instance through a sampler. During the introduction of the liquid sample into chamber 1, the flow of carrier gas is preferably interrupted.

The chamber 1 is heated by the means 12 to a temperature superior to that of boiling point of the solvent, and is such as to cause evaporation of the same and of at least part of the compounds as soon as the sample arrives into chamber 1. The temperature of chamber 1 will generally be at least 200° C. but could also reach around 350° C., to evaporate the solvent together with all the compounds. The presence of the file 3 or of the inert packing with plugs in glass wool as described above allows the evaporation front of the sample to stabilize despite the high temperature of the chamber and the high flow-rate of the sample. This stabilization is favoured if the sample is fed into chamber 1 with controlled flow. The non-volatile products remain inside chamber 1.

The vapors thus generated are thereafter made to flow through a pre-column where there is retention of the compounds of present interest in the vapors coming out of chamber 1.

In the case of FIG. 1 the vapors, comprising solvent and compounds, flow from chamber 1 to the pre-column 5, which is maintained at a lower temperature to that of the chamber 1. This temperature is sufficient to create the pressure necessary to allow the unloading of the vapors into the atmosphere, and prevent the condensation of the solvent. In other words, this temperature, which could be indicated as "dew point" is such as to allow an interaction of the vapors of solvent with the stationary phase 6 of the pre-column 5, i.e. such as to provoke a "swelling" of the stationary phase—the so-called "phase soaking"—by part of the solvent vapors and thus increase the retention power for the compounds of interest in this way, on the part of the stationary phase.

The FIG. 5 shows the chromatogram of the analysis of 600 µl of pentane containing a compound of C10–C20 alkanes, injected with flow-rate of 400 µl/min and transferred, once vaporized, to a pre-column coated with stationary phase, maintained at 48° C. to optimize the "phase soaking." In the case of FIG. 3, the vapors flow from the pre-column 5a, which is maintained at such a temperature as to guarantee the recondensation of at least part of the solvent vapors and their subsequent evaporation for the unloading from the duct 11. According to this technique, a flow of transport gas is preferably fed in this phase to the pre-column 5a to promote the evaporation of the solvent. Two advantages are derived: there is partial recondensation of the solvent, avoiding the use of very long pre-columns, and if the vapors are diluted, so the temperature at which the pre-column is maintained is reduced.

This variation, i.e. the recondensation of the vapors in a retention gap, is adopted when the sample contains volatile compounds that would not be sufficiently retained by the stationary phase of the pre-column 5. As mentioned above, the presence of liquid solvent allows, through the so-called solvent effect (solvent trapping), the trapping of the more volatile compounds.

During the solvent evaporation phase and the passage of its vapors through the pre-column 5 or 5a, the valve 9 is set to connect the duct 7 with the unloading duct 11, and the vapors leaving the pre-column 2 flow therefore through the ducts 7 and 11.

Once the phase of unloading the solvent has ended (or before, if desired in operation of the formalities of control of the functions of the gaschromatograph) the valve 9 is set to the resistance 10 to have a flow of drainage and, if fact is not already stayed, will feed the carrier gas to the vaporization chamber again.

The precolumns 5, or 5a, are therefore heated to carry the compounds to the separation column 8.

It is possible to effect the feeding of the sample to the chamber 1 in other ways, for instance through a loop with carrier gas, but the forms described above (controlled flow) have been particularly advantageous in that they have allowed fractions to be transferred with larger volumes and to identify and analyze even the more volatile compounds.

The invention will be further illustrated by the following example:

EXAMPLE I

Retention with coated pre-column and "phase soaking"

A solution has been prepared in pentane of a product with a mineral oil base consisting of C20–C26 isoalkanes of the type used in the food industry as a separator.

The concentration of the mineral oil was 0.5 µg/ml, and that of the internal standard (n-C13) was equal to 0.03 µg/ml (i.e. 30 times smaller than possible with traditional processes). 400 ul of the solution was injected into a device comprising a vaporization chamber with insert in metallic thread and a pre-column of 2 m coated with PS 255. The temperature of the vaporization chamber was of 350° C. and that of the pre-column of 50° C. during the transfer of the injected sample; there followed a programmed to 15° C./min.

The resultant chromatogram, which corresponds to a concentration of 1.5 ug of mineral oil per mg of feed fat is shown in FIG. 4.

We claim:

1. A process for the introduction of a liquid sample with large volume into a gas chromatograph, comprising the evaporation of the sample, the elimination of at least part of the vapors of the solvent present in the sample and the dispatch to a GC column of the vapors of compounds for analysis, characterized by comprising the following phases: evaporating the sample in a non-selective way in a vaporization chamber, stabilizing the evaporation front inside of said chamber; feeding the vapors generated in said chamber to a means of retention of the compounds to be analyzed located upstream of said GC column and maintained at a lower temperature to that of said vaporization chamber in order to separate said compounds from the solvent vapors; increasing the retention of the compounds of interest with said means of retention with a portion of the solvent vapors therein, unloading at least part of the solvent vapors leaving said means of retention; and sending the compounds to be analyzed by said GC column.

2. A process according to claim 1, wherein said means of retention comprises a pre-column provided with a stationary phase and said process additionally comprises maintaining said pre-column at such a temperature to prevent the condensation of the solvent vapors and to provoke a swelling of said stationary phase by a portion of the solvent vapors.

3. A process according to the claim 1 further comprising the phase of feeding the vapors leaving the said vaporization chamber to said means of retention comprising a pre-column deprived of stationary phase and of condensing there at least part of said vapors to get a solvent effect of retention of the compounds to be analyzed.

4. A process according to claim 3, additionally comprising feeding the sample to said vaporization chamber and controlling the flow-rate of said sample to said vaporization chamber.

5. A process according to claim 4, additionally comprising feeding a transport gas during at least part of the feeding of and evaporation of the sample in said vaporization chamber and interrupting the feed of said transport gas during the feeding of and evaporation of the sample in said vaporization chamber.

6. A process according to claim 5, characterized by interrupting the feed of the transport gas and that of the liquid sample to said vaporization chamber through separate valves.

7. A process according to claim 1, further comprising the phase of feeding the vapors leaving said vaporization chamber to said means of retention, wherein said means of retention comprises a pre-column deprived of a stationary phase, and of condensing at said pre-column at least part of said vapors to get a solvent effect of retention of the compounds to be analyzed;

further characterized by feeding the sample to said vaporization chamber and controlling the flow rate of said sample to said vaporization chamber;

further characterized by feeding a transport gas during at least a part of the feeding of and evaporation of the sample in said vaporization chamber, and interrupting the feed of transport gas during the feeding of and evaporation of the sample in said vaporization chamber; and further characterized by controlling the flow rate of said sample to said vaporization chamber and interrupting the feed of transport gas in said vaporization chamber through separate valves.

8. A device for the introduction of liquid samples into a gaschromatograph, comprising a vaporization chamber of the sample and a GC column, characterized by further comprising: means of retention of the compounds to be analyzed located between said vaporization chamber and said column; means of stabilization of an evaporation front of the sample inside of said vaporization chamber; and means of unloading solvent vapors leaving said means of retention of the compounds.

9. A device according to claim 8, characterized by said means of retention comprising a pre-column provided with stationary phase.

10. A device according to claim 9, characterized by comprising means for heating said vaporization chamber and said pre-column separately.

11. A device according to claim 9, said means of retention comprising a pre-column deprived stationary phase;

said means of stabilization of the evaporation front of the sample being a packing material or at least one insert being constituted by a thread or fiber in metal or in fused silica;

further comprising means for heating said vaporization and said pre-column separately; and further comprising separate means for controlling the feeding of a transport gas and of said liquid sample.

12. A device according to claim 8, characterized by said means of retention comprising a pre-column deprived of stationary phase.

13. A device according to claim 8, characterized by said means of stabilization of the evaporation front of the sample being selected between a packing material and one or more inserts.

14. A device according to claim 13, characterized by said inserts being constituted by a thread or fiber in metal or in fused silica.

15. A device according to claim 8, characterized by comprising separate means for controlling the feeding of a transport gas and of said liquid sample.

* * * * *